United States Patent [19]

Miller et al.

[11] 4,015,464
[45] Apr. 5, 1977

[54] ULTRASONIC CONTINUOUS WAVE PARTICLE MONITOR

[75] Inventors: James G. Miller, Clayton; Richard E. Clark, Richmond Heights; Mark S. Conradi; Dennis R. Dietz, both of Clayton, all of Mo.; Joseph S. Heyman, Gloucester, Va.

[73] Assignee: The Washington University, St. Louis, Mo.

[22] Filed: Feb. 21, 1975

[21] Appl. No.: 551,913

[52] U.S. Cl. .................................. 73/61 R; 73/67.1
[51] Int. Cl.² .................. G01N 29/02; G01N 15/00
[58] Field of Search ............... 73/61, 61.1, 67.1, 19

[56] References Cited

UNITED STATES PATENTS

| | | | |
|---|---|---|---|
| 2,966,056 | 12/1960 | Heller | 73/61 R |
| 3,269,172 | 8/1966 | McGaughey | 73/61 R |
| 3,283,562 | 11/1966 | Heisig et al. | 73/67.1 |
| 3,359,788 | 12/1967 | Colvin | 73/67.1 |
| 3,413,595 | 11/1968 | Babikov et al. | 73/67.5 R |
| 3,553,636 | 1/1971 | Baird | 73/61 R |
| 3,584,964 | 6/1971 | Nejame | 73/61 R |
| 3,791,200 | 2/1974 | Hayre | 73/61 R |
| 3,859,846 | 1/1975 | Asada et al. | 73/61.1 R |
| R27,786 | 10/1973 | Roth | 340/3 |

Primary Examiner—Richard E. Aegerter
Assistant Examiner—John W. Shepperd
Attorney, Agent, or Firm—Koenig, Senniger, Powers and Leavitt

[57] ABSTRACT

Apparatus for sensing particles in a fluid medium comprising an ultrasonic resonant cavity for containing a fluid medium. A first transducer on one side of the cavity continuously propagates thereacross ultrasonic compressional waves whose phase and amplitude are perturbed by the presence of particles in the fluid medium. A second transducer positioned on the opposite side of the cavity from the first transducer substantially parallel to and in registry therewith receives the ultrasonic waves and converts them to rf electric waves of the same frequency, the rf electric waves having their phases and amplitudes modulated in response to any perturbations in the ultrasonic waves. The rf waves are amplified and fedback to the first transducer thereby to establish an oscillatory circuit. An attenuator in the oscillatory circuit causes its operation to be marginally oscillatory whereby small changes in the amplitude of the rf waves caused by any perturbations in the ultrasonic waves produce relatively large changes in the amplitude thereof. A detector responsive to perturbations in the rf wave demodulates the amplified rf wave to produce signals indicative of the presence of particles in the fluid medium. Thus, enhanced sensitivity to small changes in the ultrasonic properties of the fluid medium caused by the presence of particles therein is achieved.

18 Claims, 4 Drawing Figures

ULTRASONIC CONTINUOUS WAVE PARTICLE MONITOR

BACKGROUND OF THE INVENTION

The invention described herein was made in the course of work under a grant or award from the Department of Health, Education and Welfare.

Recent medical and industrial developments have created a growing need for improvements in particle detection and analysis. In the medical area, reports of brain damage resulting from extracorporeal perfusion of blood during open heart surgery have caused heightened interest in microemboli detection. In the industrial area, the need to better perform clean room monitoring to reduce or eliminate particle contamination and the need to better detect wear particles in hydraulic fluids are but two examples of situations where improved particle sensing techniques would be beneficial.

The use of ultrasonics in particle detection has particular advantages in that detection and analytical techniques can be noninvasive and nondestructive, that is, the mode of sensing does not interfere in any way with the medium being monitored and analysis can be electronically performed. Davies in *Rapid Response Instrumentation for Particle Size Analyses Part III*; American Laboratory, Feb. 1974, P. 47, 48 discusses applications of ultrasonic sensing techniques for industrial uses, while Patterson and Kessler in *Microemboli During Cardiopulmonary Bypass Detected by Ultrasound*; Surgery, Gynecology, & Obstetrics, vol. 129, p. 505 (1969) discuss pulsed ultrasonic techniques for microemboli detection in medical situations.

Despite the advantages of ultrasonic systems, present monitoring systems, particularly those used in medical areas have disadvantages in that existing ultrasonic sensing techniques have low sensitivity to small particles, do not continuously monitor the total volume of fluid, are relatively large in physical size which results in lack of flexibility in their use, and the costs of such ultrasonic detection systems have been high.

SUMMARY OF THE INVENTION

Among the objects of the present invention may be noted the provision of apparatus which has enhanced sensitivity to the presence of small particles in a fluid medium to rapidly respond thereto; the provision of such apparatus for continuously monitoring the total volume of fluid; and the provision of such apparatus which is compact in form, flexible in use, economical in cost and high in reliability.

Briefly, apparatus of the present invention comprises an ultrasonic resonator cavity for containing a fluid medium. First transducer means on one side of the cavity continuously propagate thereacross ultrasonic compressional waves whose phase and amplitude are perturbed by the presence of particles in the fluid medium. Second transducer means positioned on the opposite side of the cavity from the first transducer means substantially parallel to and in registry therewith receive the ultrasonic waves and convert them to rf electric waves of the same frequency which have their phases and amplitudes modulated in response to any perturbations in the ultrasonic waves. Means are provided for amplifying the rf waves, and feedback means apply the amplified rf waves to the first transducer means thereby to establish an oscillatory circuit. Attenuation means in the oscillatory circuit cause its operation to be marginally oscillatory so that small changes in the amplitude of the rf waves caused by any perturbations in the ultrasonic waves produce relatively large changes in the amplitude thereof. Detection means respond to perturbations in the rf wave to demodulate the amplified rf wave to produce signals indicative of the presence of particles in the fluid medium. Thus, enhanced sensitivity to small changes in the ultrasonic properties of the fluid medium caused by the presence of particles therein is achieved.

Other objects and features will be in part apparent and in part pointed out hereinafter.

BRIEF DESCRIPTION OF THE DRAWINGS

Corresponding reference characters indicate corresponding parts throughout the several views of the drawings.

DESCRIPTION OF A PREFERRED EMBODIMENT

Figure 1:
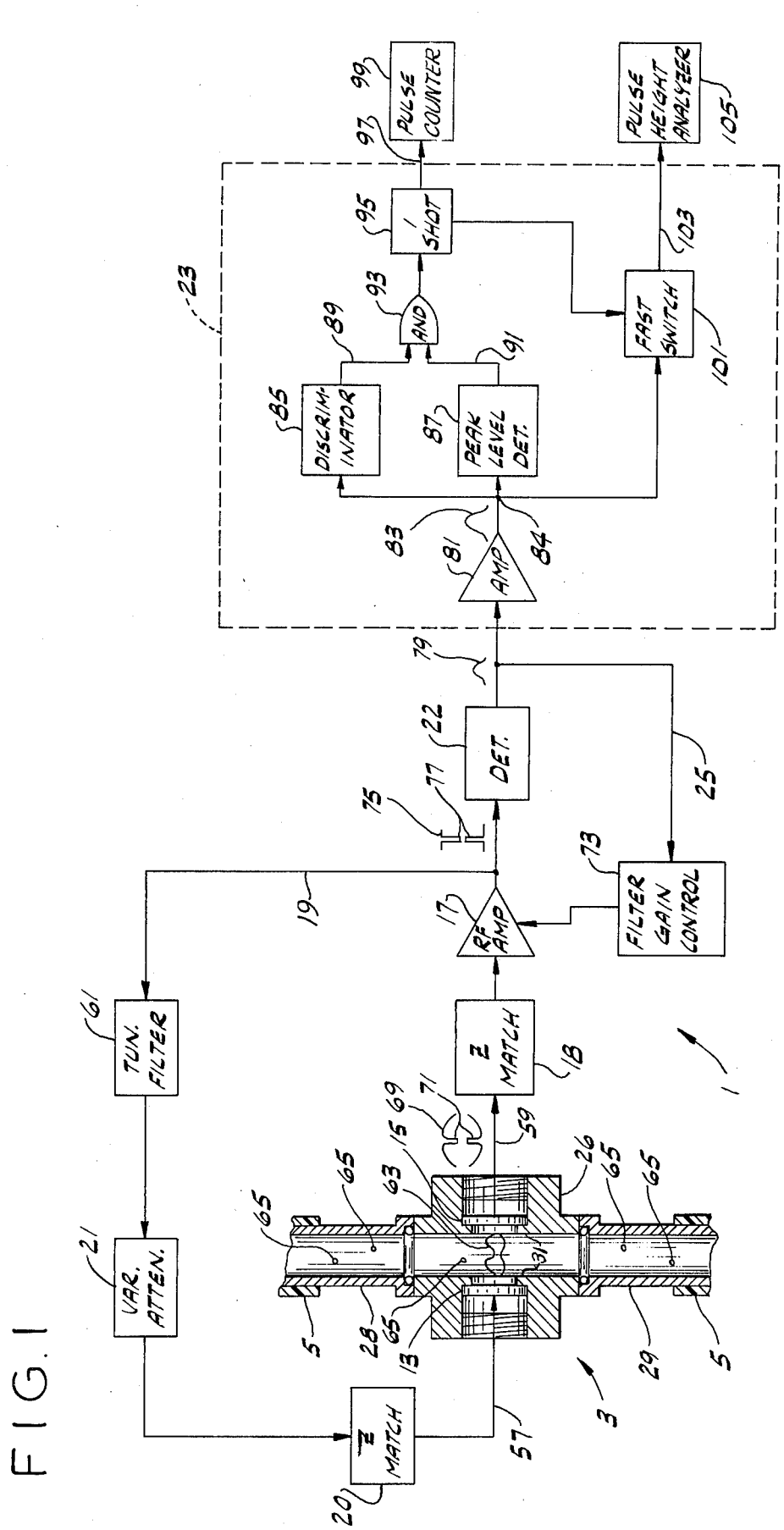
FIG. 1 is a block diagram of a continuous wave ultrasonic particle monitor of the present invention.

Referring now to the drawings and more particular to FIG. 1, a block diagram of an ultrasonic continuous wave particle monitor of the present invention is generally shown at 1. Monitor 1 includes a probe 3 which may be inserted into a fluid flow line 5. Probe 3 has inlet and outlet ports, 7 and 9 respectively, for a cavity 11 to permit the flow of a fluid medium therethrough. A pair of matched piezoelectric crystal transducers, 13 and 15 resepctively, are positioned on opposite sides of cavity 11 parallel to and in registry with each other. Crystal 13, when excited by an electric field in accordance with well known physical principals, continuously propagates across cavity 11 an ultrasonic compressional wave which is received by crystal 15 and converted, again in accordance with well known physical principals, to an rf electric wave of the same frequency. The rf electric wave is amplified by an rf amplifier 17 and fed back through circuit path 19 to provide the excitation field for crystal 13. Impedance matching networks 18 and 20 match the amplifier 17 input and output impedances with those of crystal transducers 15 and 13. The combination of the crystal transducers 13 and 15, the rf amplifier 17, and feedback path 19 establishes an oscillatory circuit whose operation is made marginally oscillatory by a variable attenuator 21 located in feedback path 19. The reason for using a marginally oscillatory circuit will be discussed hereinafter. Finally, the output of rf amplifier 17 besides being fed back on path 19 is detected by a detector 22, whose output is provided both to a signal processing network 23 and an amplifier 17 feedback circuit 25.

Figure 3:
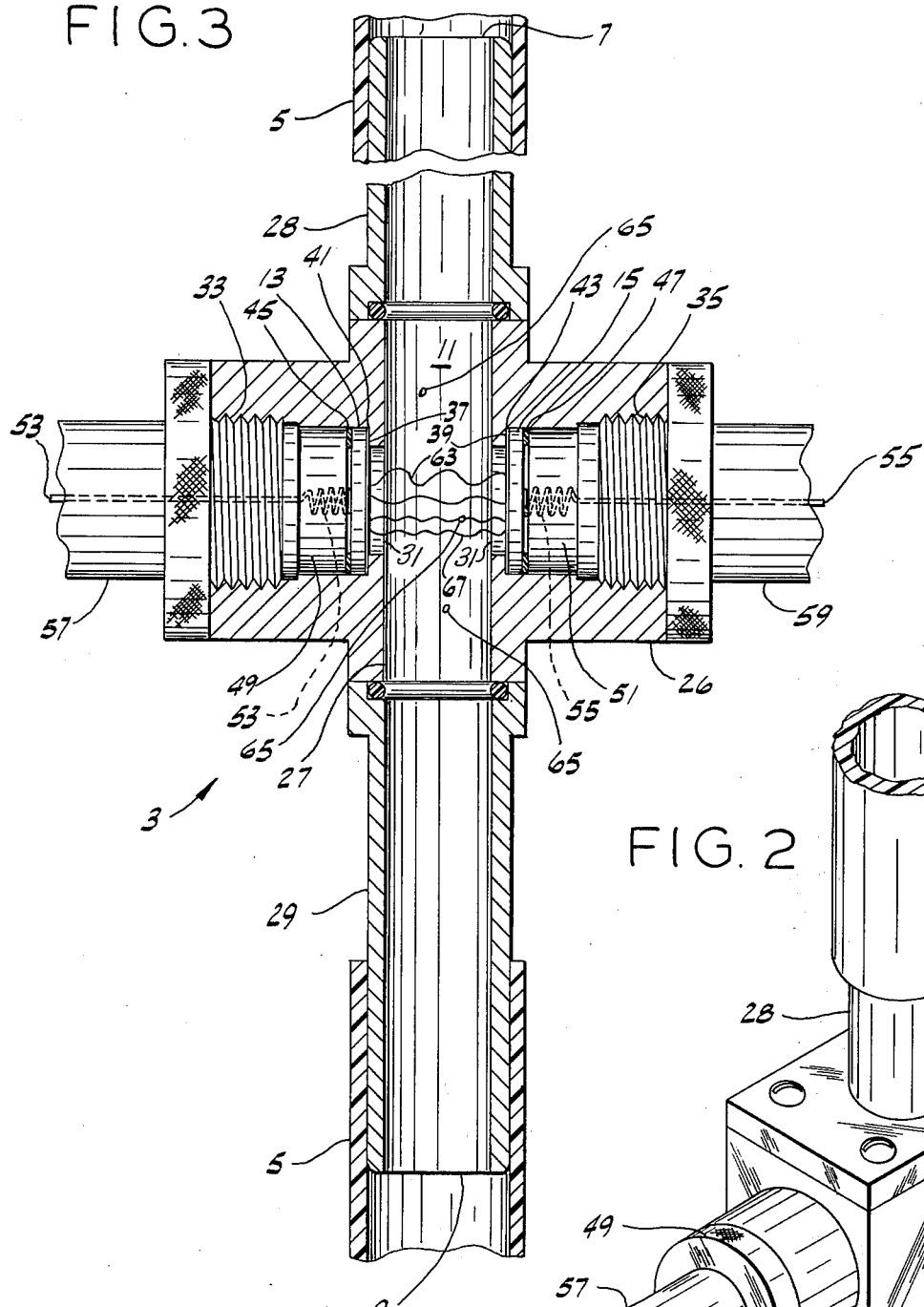
FIG. 3 is a cross-sectional view of the probe.
Figure 2:
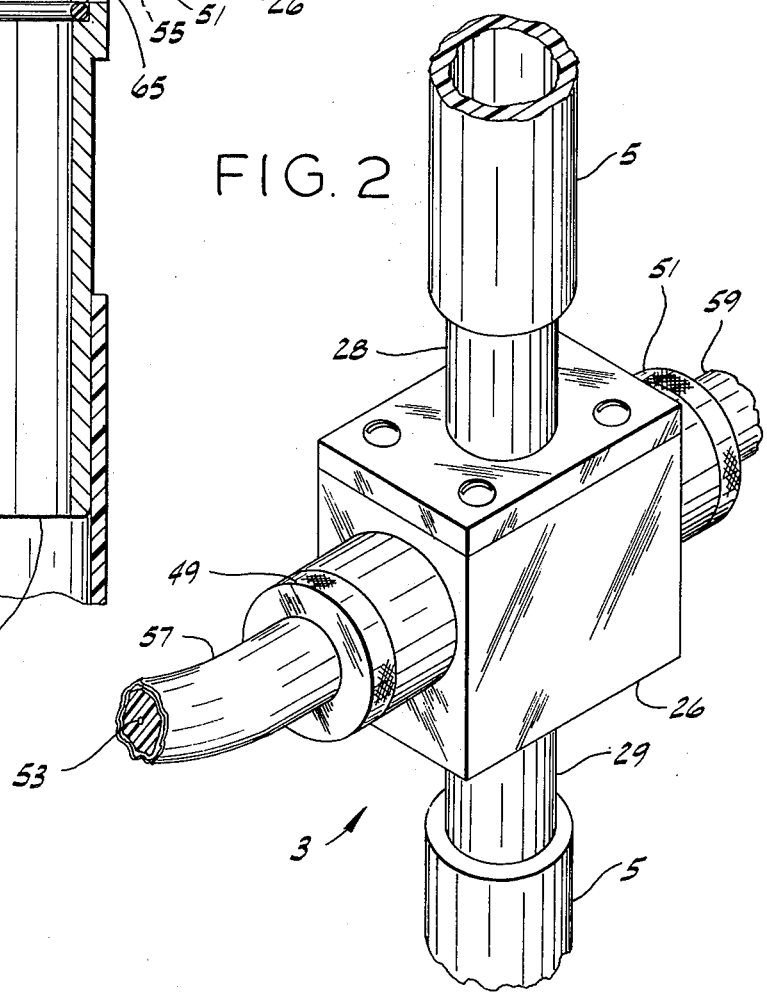
FIG. 2 is a trimetric view of a probe used in the present invention.

As shown in FIGS. 2 and 3, probe 3 includes a body portion 26 with a central bore 27 and to which are secured by machine screws flanged nipples 28 and 29 which constitute fluid inlet and outlet ports 7 and 9, for connection to fluid flow line 5. Probe body 26 has a crossbore 31 which is counterbored to form two cylindrical recesses 33 and 35, the outer ends of which are internally threaded. Crystal transducers 13 and 15 are received in these recesses and seated against ledges 37 and 39 respectively, formed at the junctions of the cross bore and the counterbores. The crossbore region constitutes resonator cavity 11 for containing the fluid medium and a transmission path between the crystals. Thin gold films 41 and 43 span the opposed apertures or openings at the inner ends of recesses 33 and 35. The films serve as electrodes for the opposed surfaces of the crystals for establishing electrical fields across each transducer in order to generate the ultrasonic compressional waves for transmission across cavity 11 by crystal 13 and the output rf electric wave by crystal 15. Films 41 and 43 further serve to isolate the fluid medium and the crystals. O-rings 45 and 47 are interposed between the outer margins of crystals 13 and 15 and the inner ends of rf coaxial connectors 49 and 51 which are threaded into recesses 33 and 35 respectively, so that spiral center conductor extensions 53 and 55 thereof can be brought into physical contact with the outer faces of crystals 13 and 15. This completes the circuits required to permit application of the rf electric field to crystal 13 to produce the ultrasonic compressional waves transmitted across cavity 11 and to pick up the electric field of excited crystal 15 to provide the rf electric waves for transmission by coaxial cable 59 as the probe 3 output.

The frequency of operation of the oscillatory circuit is a function of the natural vibratory frequency of the matched crystals 13 and 15, the dimensions of cavity 11, and the fluid medium flowing therethrough. For the circuit as shown, a closely spaced (in frequency) series of peaks or mechanical resonances are produced over a range of frequencies. A tunable filter 61, located in feedback path 19, is used to select a particular resonant frequency peak at which the oscillatory circuit is to operate. Filter 61 is a passive bandpass filter having a frequency response which is broad compared with the mechanical resonance point selected but sharp enough to distinguish between adjacent mechanical resonances. It and the ultrasonic resonator cavity 11 act as narrow bandpass filters and are lossy elements in the oscillatory circuit. Once the operating frequency peak or mechanical resonance of the circuit is established there will be no significant tendency to drift from that operation peak. Thus, this oscillatory circuit is very frequency stable without the need for frequency compensating circuits or other frequency control means.

When the monitor 1 is used, for example, during open heart surgery, its function is to detect microemboli in the blood being circulated extracorporeally and provide an indication thereof. Microemboli are any foreign or abnormal particles in the blood stream, for example, air bubbles, fat globules and blood clots. Since particles will be detected as long as their size is not smaller than the wavelength of the operating frequency, use of a 10MHZ operating frequency, for example, will permit detection of particles as small as 100 microns. Therefore, since white blood cells are 30 to 40 microns in size and red blood cells approximately 8 microns, this will insure that these cells are not detected and that anything sensed is a microembolus. In industrial applications, a higher operating frequency can be used which will permit detection of even smaller particles.

As noted, piezoelectric crystal transducer 13 continuously transmits across cavity 11 an ultrasonic compressional wave in response to a continuously applied rf electric field. This continuous transmission sets up a standing ultrasonic wave represented at 63 in FIG. 3. As can be seen, the established standing wave has a nominal amplitude and phase envelope which will be maintained as long as no particle 65 passes between crystals 13 and 15. When, however, a particle 65, shown in FIG. 3, does pass between the crystals, the standing wave envelope will be perturbed to produce a different standing wave envelope 67. The amplitude decrease or acoustic attenuation and the phase shift shown in envelope 67 result from the propagation medium for the ultrasonic compressional wave being materially altered during the passage of particle 65. The degree of effect of a particle 65 on standing wave 67 depends upon the particle size. Thus, standing wave envelope 67 is illustrative only and its alteration from standing wave 63 may be more or less pronounced.

Because an ultrasonic compressional wave is continuously generated in cavity 11, the sensitivity of the monitor system to perturbations caused by any particle 65 is greatly enhanced. This results from the numerous shadowing effects created by particle 65 as it traverses the distance in cavity 11 between the faces of crystal transducers 13 and 15. Since a standing wave envelope is produced by the transmission and reflection of mechanical energy across cavity 11 between crystals 13 and 15, a particle 65 will interfere with each transmission and reflection for the period of its traversal by obscuring a portion of the face of crystal 15 from the wave propagated by crystal 13 and obscuring a portion of the face of the crystal 13 from the wave reflected by crystal 15. Therefore, since the ultrasonic compressional wave is continuously generated by crystal 13 and reflected by crystal 15 there are many more shadowings, and the effect created by particle 65 passing between the crystals' faces is more pronounced than if a pulsed or noncontinuous wave propagtion system were employed.

The enhanced sensitivity or nonelectronic amplification of perturbations to standing wave 63 is reflected in the rf electric wave produced by crystal transducer 15 in response to the received ultrasonic compressional waves generated by crystal transducer 13. The phase and amplitude perturbations caused by particle 65 modulate the crystal 15 output rf electric wave phase and amplitude. An envelope of this rf electric wave is represented at 69 in FIG. 1. The slowly varying portion of envelope 69 is due to hydraulic noise in the fluid flow system such as that caused by pump motor operations. An amplitude variation 71 in envelope 69 results from the perturbations caused by a particle 65 and the degree of variation depends upon the size of the particle 65 detected. This variation is approximately 1/5000 of the nominal rf electric wave amplitude for a 100 micron particle and the period of amplitude variation 71 is typically between 10 and 20 milliseconds.

Since the oscillatory circuit established is marginally oscillatory, it is more sensitive to small variations in the input to amplifier 17, corresponding to amplitude variations 71 in the input electric wave amplitude and hence to the presence of particles 65 in the fluid medium, than it would be if the circuit were operated in a more stable condition. This can be understood as follows.

Gain is normally defined as the ratio of amplifier output voltage to input voltage. For small values of amplifier input voltage, a plot of amplifier gain versus input voltage is nearly linear, but as amplifier input voltage increases gain decreases because the amplifier begins to saturate. It is in the nearly linear gain versus input voltage region that the oscillatory circuit of the present invention is operated. Therefore, small variations in the rf wave amplitude caused by the particles 65 passing through cavity 11, produce relatively larger changes in the output rf wave amplitude. The increased sensitivity to particles 65 occurs because the small input voltage changes to amplifier 17 which result from amplitude variations 71 require rather large changes in output level to provide the necessary increase in gain to keep the circuit oscillatory, whereas if the oscillator were operated in a more stable condition, small amplifier input voltage changes would require only small output level changes to provide the necessary gain changes to maintain the circuit in oscillation.

Because it is desired that monitor 1 respond only to the presence of particles 65, the slowly varying rf electric wave envelope 69 amplitude due to the system operating environment is preferably eliminated. Accordingly, a filter gain control circuit 73 is positioned in the feedback loop 25 of rf amplifier 17 to provide the negative feedback necessary to cancel out these slow variations. The filter portion of circuit 73 is a low-pass filter which senses the slow amplitude variations of envelope 69 while being insensitive to the variations 71 caused by particles 65, and changes the amplifier 17 gain accordingly. The resultant amplifier 17 output rf wave envelope is represented at 75 in FIG. 1. The amplitude variations 77 in envelope 75 are the amplified result of the ultrasonic wave perturbations caused by a particle 65.

The output of amplifier 17 besides being fed back to crystal transducer 13 is also supplied to detector 22. Detector 22 is an AM demodulator circuit which responds to the amplitude variations 77 in envelope 75 to produce a demodulated output signal 79 the amplitude and width of which are dependent upon the size of the particle 65 sensed during its passage through cavity 11. Detector 22 is a field-effect transistor (FET) whose operation is well known in the art.

The output signal from detector 22, represented at 79, is fed back to amplifier 17 on path 25 for the reasons previously discussed. The detector 22 output signal is also supplied to the signal processing network 23 where it is amplified by a series of fixed and variable gain amplifiers denoted at 81, with the resultant amplified signal 83 at junction 84 being processed by a discriminator 85 and a peak level detector 87 to determine if the sensed particle 65 passing through cavity 11 was of a minimum size. If so, then signals on lines 89 and 91 to AND gate 93 produce an output to trigger a one-shot multivibrator 95 to provide an output on line 97 to a pulse counter 99. The output of amplifiers 81 is further routed to an electronic or fast switch 101 which is activated by the output of one-shot multivibrator 95 to provide a signal on line 103 to a pulse height analyzer 105 whose amplitude is equal to the peak amplitude of signal 83. Network 23, as will be discussed, is thus responsive to the detection of particles 65 to provide a first output on 97 indicative of the number of particles exceeding a minimum size, the output signal being compatible with pulse counting circuits to trigger them accordingly, and is further responsive to provide an output on 103 compatible with pulse height analyzer circuits by which the number of particles of a particular size can be determined.

Figure 4:
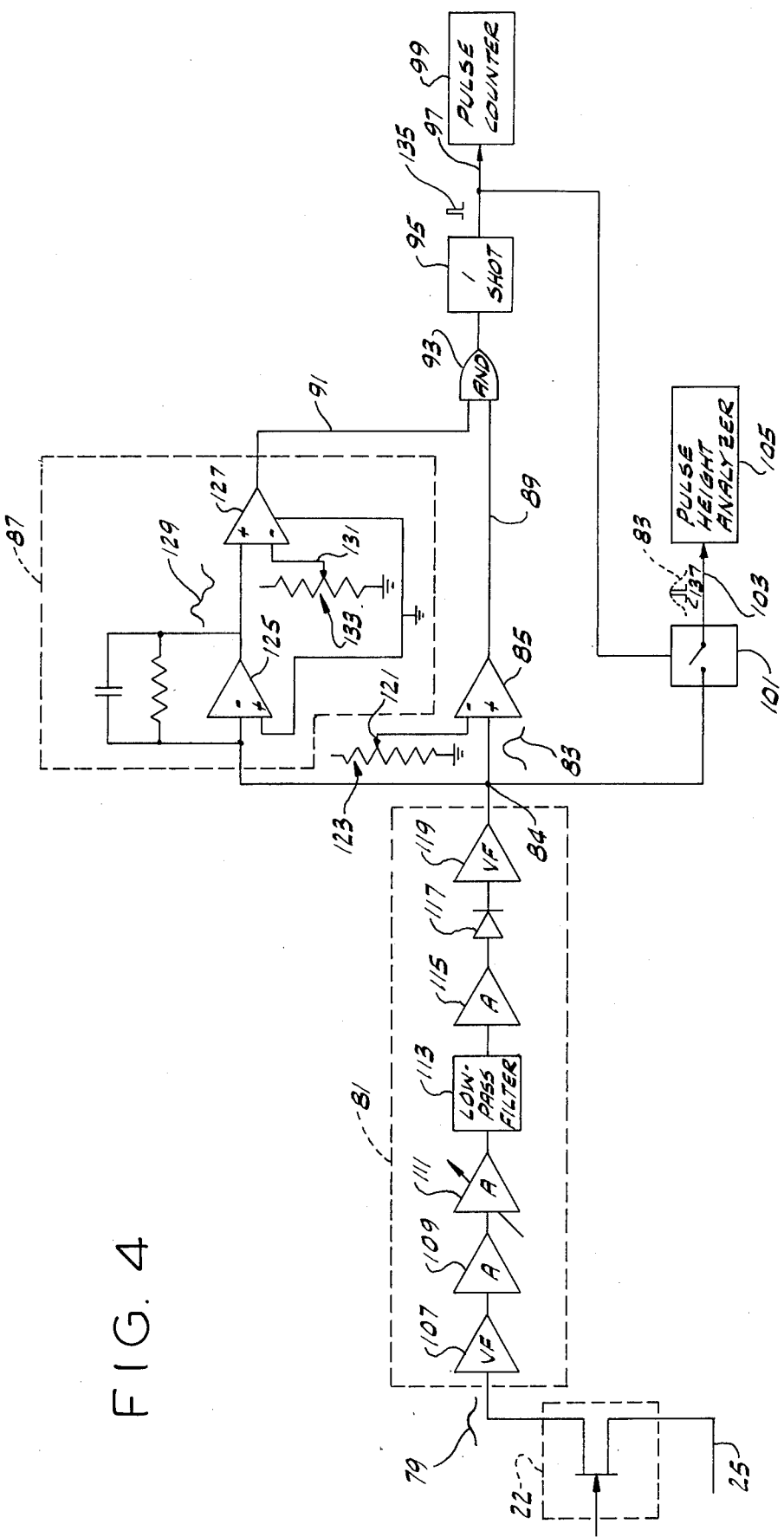
FIG. 4 is a combined block and circuit diagram of the signal processing electronics of the present invention.

Signal processing network 23 is shown in more detail in FIG. 4. As shown, the amplifier 81 network includes a first voltage follower 107 which provides signal isolation, a fixed and a variable gain amplifier, 109 and 111, respectively, a low pass filter 113, another fixed gain amplifier 115, a diode 117, and a second voltage follower 119 also for providing isolation. The fixed gain amplifiers 109 and 115 provide 30 db of amplification, while the total network gain is controlled by the setting of the amplifier 111 gain. Filter 113 is an operational amplifier used as an active low-pass filter and has a cutoff frequency of 150Hz. This is to eliminate noise. Diode 117 is an ideal diode which provides a negative output when its input is positive and a zero output when its input is negative thus eliminating any signal overshoot past a zero reference level.

The amplifier network output signal 83 is processed, as noted, by discriminator 85 and a peak level detector 87. Discriminator 85 is sensitive to the amplitude of signal 83 exceeding a predetermined minimum level to provide an output to AND gate 93 on line 89. This minimum level corresponds to the minimum size of a detected particle 65 which is desired to be monitored, and this level is established as the discriminator 85 reference by the positioning of a wiper arm 121 along a potentiometer 123. With the reference level established, any input signal 83 whose amplitude exceeds the minimum level established causes discriminator 85 to supply an output to AND gate 93 via line 89. Peak detector 87 senses when a signal 83 is at its peak level or maximum amplitude and provides an output to AND gate 93 on line 91. A signal differentiator 125 and an operational amplifier (op-amp) 127 perform the peak level detection. Differentiator circuits such as 125 are well known and supply a signal 129 to the op-amp 127 in response to input signal 83. Op-amp 127 is configured to provide an output on line 91 to AND gate 93 whenever the level of signal 129 begins to go negative which corresponds to the beginning of the fall-off from the peak amplitude of signal 83. The reference level of op-amp 127 is established by the positioning of a wiper arm 131 along a potentiometer 133.

AND gate 93 normally has a logic low output level. This level will go high, however, when gate 93 has coincident input signals from discriminator 85 and peak level detector 87 thereby indicating that a particle 65 exceeds a minimum size and that the signal generated in response to the presence of that particle is at a peak amplitude value. A high level gate 93 output will trigger one-shot multivibrator 95 to generate a 20 microsecond pulse 135 which is compatible with pulse counting circuits. This pulse will trigger the aforementioned pulse counting circuit to provide a visual or other indication that particles exceeding a predetermined minimum size are present in the fluid medium. Thus, during open heart surgery where there is extracorporeal flow of blood, such an indication would alert the operating surgeon to have perfusion filters inserted in the flow line to remove these particles from the blood supply and prevent possible injury to the patient.

In a laboratory or industrial setting where it would be advantageous to know the number of particles of a particular size present in the fluid medium, a pulse height analyzer 105 may be utilized. To provide inputs for such a unit, the output of one-shot multivibrator 95 is used to actuate fast-switch 101. Fast switch 101 is an electronic switch, which is engaged for the duration of the pulse supplied by multivibrator 95 which is 20 microseconds. Signal 83 is supplied coincidentally to fast switch 101, discriminator 85, and peak detector 87. Peak detector 87 supplies an input to AND gate 93 only when signal 83 has attained its peak amplitude, and correspondingly, switch 101 is actuated when the amplitude of signal 83 applied to the switch 101 input is at its peak amplitude value. Thus, the switch 101 output is a 20 microsecond pulse 137 whose amplitude corresponds to the peak amplitude of signal 83 or the size of detected particle 65, and whose pulse duration is compatible with pulse height analyzer circuits. Further, because particles in a wide range of sizes may be present in the fluid medium, the signals 83 may have a wide range of amplitude values which may make signal processing difficult. To aid in processing, a logarithmetic amplifier (not shown) may be positioned between the amplifier network 81 output and point 84. Such an amplifier will compress a wide range of amplitude values into a narrower, reduced range of values and thus facilitate further signal processing.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. Apparatus for sensing particles in a fluid medium comprising:
    an ultrasonic resonator cavity for containing a fluid medium;
    first transducer means on one side of the cavity for continuously propagating thereacross ultrasonic compressional waves whose phase and amplitude are perturbed by the presence of particles in the fluid medium;
    second transducer means positioned on the opposite side of the cavity from the first transducer means substantially parallel to and in registry therewith for receiving the ultrasonic waves and converting them to rf electric waves of the same frequency and whose phases and amplitudes are modulated in response to any perturbations in the ultrasonic waves;
    means for amplifying the rf waves;
    feedback means for applying the amplified rf waves to the first transducer means thereby to establish a self-excited continuous wave oscillatory circuit;
    attenuation means in the circuit for causing its operation to be marginally oscillatory whereby small changes in the amplitude of the rf waves caused by any perturbations in the ultrasonic waves produce relatively large changes in the amplitude thereof; and
    detection means responsive to perturbations in the rf wave for demodulating the amplified rf wave to produce signals indicative of the presence of particles in the fluid medium whereby enhanced sensitivity to small changes in the ultrasonic properties of the fluid medium caused by the presence of particles therein is achieved.

2. Apparatus as set forth in claim 1 wherein the ultrasonic resonator cavity has an inlet and an outlet whereby a fluid medium may flow through the cavity.

3. Apparatus as set forth in claim 1 wherein the detection means is an A.M. demodulator circuit responsive to perturbations in the rf wave amplitude.

4. Apparatus as set forth in claim 1 wherein the first and second transducer means are matched piezoelectric crystals, the resonant frequency of the oscillatory circuit being a function of the natural vibratory frequency of said crystals, the dimensions of the cavity, and the fluid therein.

5. Apparatus as set forth in claim 4 wherein the oscillatory circuit further includes means for matching the input and output impedance of the amplifying means to that of the piezoelectric crystals.

6. Apparatus as set forth in claim 1 wherein the oscillatory circuit further includes a tunable filter for selecting the operating resonant frequency of the circuit and suppressing other resonant frequencies.

7. Apparatus as set forth in claim 1 wherein the amplification means includes an automatic level control means responsive to relatively slow variations in the rf wave amplitude whereby an rf wave of an amplitude which is substantially constant except for amplitude perturbations caused by the presence of particles in the fluid medium is maintained.

8. Apparatus as set forth in claim 7 wherein the level control means comprises a feedback loop having an automatic voltage control circuit with a low-pass filter.

9. Apparatus as set forth in claim 1 further including processing means for indicating the presence of particles exceeding a predetermined minimum size as a function of the amplitude of modulation caused by any perturbations.

10. Apparatus as set forth in claim 9 further including a discriminator circuit responsive to the signals from the detection means to provide an output when the amplitude of a signal exceeds a predetermined minimum level indicative of the smallest size particle to be sensed.

11. Apparatus as set forth in claim 9 further including a circuit responsive to the signals from the detection means to provide an output when the amplitude of a signal is at its peak level.

12. Apparatus as set forth in claim 11 further including a discriminator circuit responsive to the signals from the detection means to provide an output when the amplitude of a signal exceeds a predetermined minimum level, and an AND gate responsive to the outputs from the discriminator circuit and peak level detector circuit to provide an output signal indicative of the presence of particles in the fluid medium which exceed a predetermined minimum size.

13. Apparatus as set forth in claim 12 further including a one-shot multivibrator circuit responsive to a signal from the AND gate to provide an output signal to a display means to indicate that a particle of a minimum size has been sensed in the fluid medium.

14. Apparatus as set forth in claim 13 further including a fast switch responsive to the output of the one-shot multivibrator circuit to pass signals from the detection means, and analyzer means responsive to signals from the detection means passed by the fast switch to determine how many particles of a particular size have been sensed in the fluid medium.

15. A method of sensing discrete particles in a fluid medium comprising:
    continuously generating by a first transducer ultrasonic compressional waves in an ultrasonic resonator cavity having a second transducer means positioned on the opposite side of the cavity from the first transducer;
    converting the ultrasonic waves received by the second transducer into rf electric waves of the same frequency;

amplifying the rf electric waves for feedback to the first transducer to establish a self-excited oscillatory resonant circuit;

attenuating the amplified rf waves to make said circuit marginally oscillatory;

causing the phase and amplitude of the compressional waves to be perturbed by passing particles through the ultrasonic resonator cavity containing the fluid medium, the phases and amplitudes of the rf electric waves being modulated in response to such perturbations in the ultrasonic compressional waves with the small changes in the amplitude of rf waves resulting from said perturbations causing an increase in amplification gain by marginal oscillatory action thereby to maintain the circuit in oscillation; and detecting the modulated amplified rf waves to produce signals responsive to the perturbations in the rf waves and indicative of the presence of discrete particles in the fluid medium whereby enhanced sensitivity to small changes in the ultrasonic properties of the fluid medium caused by the presence of particles therein is achieved.

16. A method as set forth in claim 15 which includes the further step of electronically processing the detected signals to indicate the presence of particles exceeding a predetermined minimum size as a function of the amplitude of modulation caused by said perturbations.

17. A method as set forth in claim 16 in which the electronic processing step includes discriminating between signals of different amplitudes to provide an indication of the passage of only particles which exceed a predetermined minimum size.

18. A method as set forth in claim 17 which includes the further step of sensing signals representative of particles in at least two different ranges of size above said predetermined minimum size and indicating the numbers of particles in each of said ranges.

* * * * *

UNITED STATES PATENT OFFICE
CERTIFICATE OF CORRECTION

Patent No. 4,015,464     Dated April 5, 1977

Inventor(s) James G. Miller et al

It is certified that error appears in the above-identified patent and that said Letters Patent are hereby corrected as shown below:

On the cover sheet Item (73), the assignee should read:

-- said Miller, Clark, Conradi and Dietz, assors to The Washington University, St. Louis, Mo. --.

Signed and Sealed this

Twentieth Day of September 1977

[SEAL]

Attest:

RUTH C. MASON
*Attesting Officer*

LUTRELLE F. PARKER
*Acting Commissioner of Patents and Trademarks*